US006913885B2

(12) United States Patent
Sklar et al.

(10) Patent No.: US 6,913,885 B2
(45) Date of Patent: Jul. 5, 2005

(54) ASSOCIATION OF DOPAMINE BETA-HYDROXYLASE POLYMORPHISMS WITH BIPOLAR DISORDER

(75) Inventors: Pamela Sklar, Brookline, MA (US); Eric S. Lander, Cambridge, MA (US); Melvin G. McInnis, Timonium, MD (US); J. Raymond DePaulo, Jr., Baltimore, MD (US); Virginia Willour, Baltimore, MD (US); James Potash, Baltimore, MD (US)

(73) Assignees: Whitehead Institute for Biomedical Research, Cambridge, MA (US); Johns Hopkins University, Baltimore, MD (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 10/054,678

(22) Filed: Jan. 22, 2002

(65) Prior Publication Data
US 2003/0027172 A1 Feb. 6, 2003

Related U.S. Application Data

(63) Continuation of application No. 09/852,967, filed on May 10, 2001, now abandoned.
(60) Provisional application No. 60/202,910, filed on May 10, 2000.

(51) Int. Cl.[7] .......................... C12Q 1/68; C07H 21/02; C07H 21/04
(52) U.S. Cl. ........................ 435/6; 536/23.1; 536/23.5; 536/24.31; 536/24.33
(58) Field of Search .................... 435/6, 91.2; 536/23.1, 536/23.5, 24.31, 24.33

(56) References Cited

PUBLICATIONS

Cubells et al. American Journal of Medical Genetics (1997) 74: 374–379.*
Cubells et al. Molecular Psychiatry (2000) 5: 56–63).*
Kirov et al. Molecular Psychiatry (1999) 4: 558–565).*
Williams et al. American Journal of Medical Genetics (1999) 88:557–559).*
Cubells (Society for Neuroscience Abstracts. Nov. 2000. 26(1–2): p. 1161, abstract 436.1.*
Houy et al. American Journal of Human Genetics. Aug. 2000. 96: 528, abstract P208.*
Iwata et al. American Journal of Medical Genetics. Jan. 2003. 116B:23–26.*
Payton et al. American Journal of Medical Genetics (2001) 105: 464–470.*
Cubells, J.F., et al., "Genotype—controlled Analysis of Plasma Dopamine Beta–hydroxylase Activity in Unipolar Psychotic Depression," *Society for Neuroscience Abstracts*, 26:436.1 (2000).
De bruyn, A., et al., "A Linkage Study Between Bipolar Disorder and Genes Involved in Dopaminergic and GABAergic Neurotransmission," *Psychiatric Genetics*, 6:67–73 (1996).
Hamner, M.B., et al., "Plasma Dopamine Beta–hydroxylase Activity in Psychotic and Non–psychotic Post–traumatic Stress Disorder," *Psychiatry Research*, 77:175–181 (1998).
Kirov, G., et al., "Family–based Association Studies of Bipolar Disorder with Candidate Genes Involved in Dopamine Neurotransmission: DBH, DAT1, COMT, DRD2, DRD3 and DRD5," *Molecular Psychiatry*, 4:558–565 (1999).
Kobayashi, K., et al., "Human Dopamine Beta–hydroxylase Gene: Two MRNA Types Having Different 3'–Terminal Regions are Produced Through Alternative Polyadenylation," *Nucleic Acids Research*, 17:1089–1102 (Feb., 1989).
Lamouroux, A., et al., "The Primary Structure of Human Dopamine–β–hydroxylase: Insights into the Relationship Between the Soluble and the Membrane–bound Forms of the Enzyme," *The EMBO Journal*, 6:3931–3937 (1987).
Mód, L., et al., "Serum DBH Activity in Psychotic vs. Nonpsychotic Unipolar and Bipolar Depression," *Psychiatry Research*, 19:331–333 (1986).

* cited by examiner

Primary Examiner—Carla J. Myers
(74) Attorney, Agent, or Firm—Fish & Neave IP Group; Ropes & Gray LLP

(57) ABSTRACT

A central role for the gene encoding dopamine beta-hydroxylase in neuropsychiatric disorders is disclosed. Use of single nucleotide polymorphisms in the dopamine beta-hydroxylase gene for diagnosis, prediction of clinical course and treatment response, development of new treatments and development of cell-culture based and animal models for research and treatment are disclosed.

4 Claims, 4 Drawing Sheets

1 : NM_000787 . Homo sapiens        PubMed, Protein, Related Sequences,
dopam...[gi:4503260]                                                LinkOut

```
LOCUS       NM_000787    2725 bp    mRNA          PRI       19-MAR-1999
DEFINITION  Homo sapiens dopamine beta-hydroxylase (dopamine
            beta-monooxygenase) (DBH) mRNA.
ACCESSION   NM_000787
VERSION     NM_000787.1  GI:4503260
KEYWORDS    .
SOURCE      human.
  ORGANISM  Homo sapiens
            Eukaryota; Metazoa; Chordata; Craniata; Vertebrata; Mammalia;
            Eutheria; Primates; Catarrhini; Hominidae; Homo.
REFERENCE   1  (bases 1 to 2725)
  AUTHORS   Kobayashi,K., Kurosawa,Y., Fujita,K. and Nagatsu,T.
  TITLE     Human dopamine beta-hydroxylase gene: two mRNA types having
            different 3'-terminal regions are produced through alternative
            polyadenylation
  JOURNAL   Nucleic Acids Res. 17 (3), 1089-1102 (1989)
  MEDLINE   89160241
REFERENCE   2  (bases 1 to 2725)
  AUTHORS   Nagatsu,T.
  TITLE     Direct Submission
  JOURNAL   Submitted (14-OCT-1988) Nagatsu T., Department of Biochemistry,
            Nagoya University, School of Medicine, Nagoya 466, Japan
COMMENT     REFSEQ: This reference sequence was derived from X13255.
            see also X13256 for type b mRNA
            Map data from Craig et al. Cytogenet. Cell Genet. 48:48-50(1988).
            PROVISIONAL RefSeq: This is a provisional reference sequence
record
            that has not yet been subject to human review. The final curated
            reference sequence record may be somewhat different from this one.
FEATURES             Location/Qualifiers
     source          1..2725
                     /organism="Homo sapiens"
                     /db_xref="taxon:9606"
                     /map="9q34"
     gene            1..2725
                     /gene="DBH"
                     /db_xref="LocusID:1621"
                     /db_xref="MIM:223360"
     CDS             33..1844
                     /gene="DBH"
                     /EC_number="1.14.17.1"
                     /codon_start=1
                     /db_xref="LocusID:1621"
                     /db_xref="MIM:223360"
                     /product="dopamine beta-hydroxylase (dopamine
                     beta-monooxygenase)"
                     /protein_id="NP_000778.1"
                     /db_xref="GI:4503261"
```

/translation="MREAAFMYSTAVAIFLVILVAALQGSAPRESPLPYHIPLDPEGS

LELSWNVSYTQEAIHFQLLVRRLKAGVLFGMSDRGELENADLVVLWTDGDTAYFADAW

SDQKGQIHLDPQQDYQLLQVQRTPEGLTLLFKRPFGTCDPKDYLIEDGTVHLVYGILE

Figure 1A

EPFRSLEAINGSGLQMGLQRVQLLKPNIPEPELPSDACTMEVQAPNIQIPSQETTYWC

YIKELPKGFSRHHIIKYEPIVTKGNEALVHHMEVFQCAPEMDSVPHFSGPCDSKMKPD

RLNYCRHVLAAWALGAKAFYYPEEAGLAFGGPGSSRYLRLEVHYHNPLVIEGRNDSSG

IRLYYTAKLRRFNAGIMELGLVYTPVMAIPPRETAFILTGYCTDKCTQLALPPSGIHI

FASQLHTHLTGRKVVTVLVRDGREWEIVNQDNHYSPHFQEIRMLKKVVSVHPGDVLIT

SCTYNTEDRELATVGGFGILEEMCVNYVHYYPQTQLELCKTAVDAGFLQKYFHLINRF

NNEDVCTCPQASVSQQFTSVPWNSFNRDVLKALYSFAPISMHCNKSSAVRFQGEWNLQ

PLPKVISTLEEPTPQCPTSQGRSPAGPTVVSIGGGKG"

```
     sig_peptide    33..107
     mat_peptide    108..1841
                    /product="dopamine beta-hydroxylase (dopamine
                    beta-monooxygenase)"

BASE COUNT      533 a       901 c      774 g       517 t
ORIGIN
        1 tcagtcgctg ggccagcctg cccggcccca gcatgcggga ggcagccttc atgtacagca
       61 cagcagtggc catcttcctg gtcatcctgg tggccgcact gcagggctcg gctcccgtg
      121 agagcccct  ccctatcac  atccccctgg acccggaggg gtccctggag ctctcatgga
      181 atgtcagcta cacccaggag gccatccatt tccagctcct ggtgcggagg ctcaaggctg
      241 gcgtcctgtt tgggatgtcc gaccgtggcg agcttgagaa cgcagatctc gtggtgctct
      301 ggaccgatgg ggacactgcc tattttgcgg acgcctggag tgaccagaag gggcagatcc
      361 acctggatcc ccagcaggac taccagctgc tgcaggtgca gaggacccca gaaggcctga
      421 ccctgctttt caagaggccc tttggcacct gcgaccccaa ggattacctc attgaagacg
      481 gcactgtcca cttggtctac gggatcctgg aggagccgtt ccggtcactg gaggccatca
      541 acggctcggg cctgcagatg gggctgcaga gggtgcagct cctgaagccc aatatccccg
      601 aaccggagtt gccctcagac gcgtgcacca tggaggtcca agctcccaat atccagatcc
      661 ccagccagga gaccacgtac tggtgctaca ttaaggagct tccaaagggc ttctctcggc
      721 accacattat caagtacgag cccatcgtca ccaagggcaa tgaggccctt gtccaccaca
      781 tggaagtctt ccagtgcgcc cccgagatgg acagcgtccc ccacttcagc gggccctgcg
      841 actccaagat gaaacccgac cgcctcaact actgccgcca cgtgctggcc gcctgggccc
      901 tgggtgccaa ggcattttac tacccagagg aagccggcct tgccttcggg ggtccagggt
      961 cctccagata tctccgcctg gaagttcact accacaaccc actggtgata gaaggacgaa
     1021 acgactcctc aggcatccgc ttgtactaca gccaagct  gcggcgcttc aacgcgggga
     1081 tcatggagct gggactggtg tacacgccag tgatggccat tccaccacgg agaccgcct
     1141 tcatcctcac tggctactgc acggacaagt gcacccagct ggcactgcct ccctccggga
     1201 tccacatctt cgcctctcag ctccacacac acctgactgg gagaaaggtg gtcacagtgc
     1261 tggtccggga cggccgggag tgggagatcg tgaaccagga caatcactac agccctcact
     1321 tccaggagat ccgcatgttg aagaaggtcg tgtcggtcca tccgggagat gtgctcatca
     1381 cctcctgcac gtacaacacg gaagaccggg agctggccac agtgggggc ttcgggatcc
     1441 tggaggagat gtgtgtcaac tacgtgcact actacccca gacgcagctg agctctgca
     1501 agacggctgt ggacgccggc ttcctgcaga gtacttcca cctcatcaac aggttcaaca
     1561 acgaggatgt ctgcacctgc cctcaggcgt ccgtgtctca gcagttcacc tctgttccct
     1621 ggaactcctt caaccgcgac gtactgaagg ccctgtacag cttcgcgccc atctccatgc
     1681 actgcaacaa gtcctcagcc gtccgcttcc agggtgaatg gaacctgcag cccctgccca
     1741 aggtcatctc cacactggaa gagcccaccc cacagtgccc caccagccag ggccgaagcc
```

Figure 1B

```
1801 ctgctggccc caccgttgtc agcattggtg ggggcaaagg ctgagggggg acctactcct
1861 ccccctcctc catgctgtcc ctgtgggctc acaccggcac tgtgcactct actctgcgac
1921 gatccccatg aacagccct gcacgcccag gatgaagggg ccagaccacg ccctgcctg
1981 agaccacggt ccaatccagc cttcttcccc cagggtcccc tgcatggctg agagggtgtg
2041 ggtgccctgt tgacctaccc tggaccgagt ggaccacgac ctcgtccatt taaacccggc
2101 tgactcagtg cagggacagc ccgcacagtg gtccagggtc cagccctccg ccagccctgt
2161 tccgcctcac tgggtgtggc ctggcttctg ggacaggcac catgctgggc cggggtgtgg
2221 aatcaccggg aacgcccccg ccccgcccc gctgctcccg gtgtgcagcg ggtgcgggtg
2281 ccgcttaaac atttccctgc tgagtggctc gtgtttcaca gtgggcggct tccctgcgac
2341 ggaggcagga ccaggcattt agctagttag agactcgcct gggaaattgc tccattcctg
2401 agtaaacaga tattttcgcc cacctaaagg aagccctga caacaactat caccaaaaga
2461 cgaggcggca aagatccagc ggggcttctg ggcgccggtt ccacgtgggg tggaattatt
2521 agcaccagct tgcttctctg ccggtggggc cagcgctgaa cagaccgggg tggagtcagg
2581 gctgtgcttt ccgcgtggtt ctgccactta gggagtgtgc cttgggcggg ccatttcaca
2641 ttcctgaccc tcacttttct catctgtaaa accaggctga tgccgtgcgg gctaatgagc
2701 caataaagct cacacttggg ctggc
```

Figure 1C

SUMMARY OF DBH ASSOCIATION

| Original study | Transmitted | Untransmitted | Chi-sq | p-val |
|---|---|---|---|---|
| DBHu2 | 28 | 21 | 0.53 | 0.4658 |
| DBHu1 | 18 | 12 | 1.20 | 0.2733 |
| DBHp444a | 56 | 41 | 2.32 | 0.1278 |
| Replication/DePaulo | | | | |
| DBHu2 | 14 | 8 | 1.64 | 0.2008 |
| DBHu1 | 11 | 13 | 0.17 | 0.6831 |
| DBHp444a | 49 | 38 | 1.39 | 0.2383 |
| Totals | | | | |
| DBHu2 | 40 | 29 | 1.75 | 0.1854 |
| DBHu1 | 29 | 26 | 0.30 | 0.5862 |
| DBHp444a | 105 | 79 | 3.67 | 0.0553 |

DBH HAPLOTYPE ANALYSIS

| Original Study | Transmitted | Untransmitted | Chi-sq | p-val |
|---|---|---|---|---|
| Allele1 from DBHu2 and u1 | 37 | 22 | 3.81 | 0.0508 |
| Allele1 from DBHu2 and DBHp444a | 45 | 29 | 3.46 | 0.0629 |
| Allele1 from DBHu1 and DBHp444a | 43 | 23 | 6.06 | 0.0138 |
| Allele1 from all three SNPs | 46 | 25 | 6.21 | 0.0127 |
| Replication/DePaulo | | | | |
| Allele1 from DBHu2 and u1 | 19 | 11 | 1.69 | 0.1936 |
| Allele1 from DBHu2 and DBHp444a | 32 | 14 | 7.04 | 0.0080 |
| Allele1 from DBHu1 and DBHp444a | 31 | 16 | 4.79 | 0.0287 |
| Allele1 from all three SNPs | 31 | 11 | 9.52 | 0.0020 |
| Totals | | | | |
| Allele1 from DBHu2 and u1 | 55 | 33 | 5.50 | 0.0190 |
| Allele1 from DBHu2 and DBHp444a | 77 | 43 | 9.63 | 0.0019 |
| Allele1 from DBHu1 and DBHp444a | 74 | 39 | 10.84 | 0.0010 |
| Allele1 from all three SNPs | 77 | 36 | 14.88 | 0.0001 |

FIG. 2

ASSOCIATION OF DOPAMINE BETA-HYDROXYLASE POLYMORPHISMS WITH BIPOLAR DISORDER

RELATED APPLICATION

This application is a continuation of U.S. application Ser. No. 09/852,967, filed on May 10, 2001, now abandoned, which claims the benefit of U.S. Provisional Application No. 60/202,910, filed on May 10, 2000, the entire teachings of which are incorporated herein by reference.

BACKGROUND OF THE INVENTION

Modem psychiatry typically subdivides mood disorders into bipolar disorders (episodes of mania or both mania and depression) and unipolar depressive disorder (episodes of depression). Symptoms of mania include expansive, elevated or irritable mood, inflated self-esteem, grandiosity, decreased need for sleep, increased talkativeness, racing thoughts, distractibility, increased goal-directed activity, and excessive involvement in pleasurable activities with a high potential for painful consequences. Depressive symptoms include depressed mood, diminished interest or pleasure in activities, insomnia or hypersomnia, psychomotor agitation or retardation, fatigue or loss of energy, feelings of worthlessness, excessive guilt, inability to concentrate or act decisively, and recurrent thoughts of death or suicide. Several mental disorders have been proposed as alternate expressions of a bipolar genotype, including variants of schizoaffective disorder, recurrent unipolar depression and hypomania (bipolar II disorder).

Neuropsychiatric disorders, such as schizophrenia, attention deficit disorders, schizoaffective disorders, bipolar disorders and unipolar disorders, differ from neurological disorders in that anatomical or biochemical pathologies are readily detectable for the latter but not the former. Largely as a result of this difference, drugs which have been used to treat individuals with neuropsychiatric disorders, including lithium salts, valproic acid and carbamazepine, have not been predictably effective in treatment regimens across a variety of patients. Treatment regimens are further complicated by the fact that clinical diagnosis currently relies on clinical observation and subjective reports. Identification of the anatomical or biochemical defects which result in neuropsychiatric disorders is needed in order to effectively identify these disorders and to allow the design and administration of effective therapeutics for these disorders.

SUMMARY OF THE INVENTION

Work described herein relates to the discovery of an association between the dopamine beta-hydroxylase (DBH) gene and neuropsychiatric disorders, particularly bipolar disorder. Specifically, it has been discovered that a haplotype formed by alleles of three single nucleotide poymorphisms (SNPs) in the coding region of the DBH gene is transmitted significantly more often from parents to children with bipolar disorder than would be expected by chance. In the first study of 133 trios formed by a bipolar proband and his or her parents, a haplotype formed by the more common (reference) allele of each of three SNPs (DBHu1, DBHu2 and DBHp444a) was transmitted from heterozygous parents (46/25) with a p-value of 0.01. A similar result has been observed in a second sample of 83 trios for the identical haplotype with a p-value of 0.002.

The relevant SNPs in the DBH gene, with reference to SEQ ID NO: 1 shown in FIG. 1, are as follows:

DBHu1: a change from G (reference nucleotide) to T (alternate nucleotide) at nucleotide position 942, resulting in a missense amino acid mutation from alanine (reference amino acid) to serine (alternate amino acid) at amino acid 304;

DBHu2: a change from C (reference nucleotide) to T (alternate nucleotide) at nucleotide position 1635, resulting in a missense amino acid alteration from arginine (reference nucleotide) to cysteine (reference amino acid) at amino acid 535; and DBHp444a: a change from A (reference nucleotide) to G (alternate nucleotide) at nucleotide position 476, which is a silent mutation resulting in no change in amino acid sequence (glutamine at amino acid 148).

Thus, the invention relates to the SNPs identified as described herein, both singly and in combination, as well as to the use of these SNPs, and others in linkage disequilibrium with these SNPs, for diagnosis, prediction of clinical course and treatment response for neuropsychiatric disorders, development of new treatments for neuropsychiatric disorders based upon comparison of the variant and normal versions of the gene or gene product, and development of cell-culture based and animal models for research and treatment of neuropsychiatric disorders. The invention further relates to novel compounds and pharmaceutical compositions for use in the diagnosis and treatment of such disorders.

The invention further relates to a method of diagnosing or aiding in the diagnosis of a disorder (e.g., a neuropsychiatric disorder) associated with the presence of one or more of (a) a G at nucleotide position 942 of SEQ ID NO: 1; (b) a C at nucleotide position 1635 of SEQ ID NO: 1; and (c) an A at nucleotide position 476 of SEQ ID NO: 1 in an individual. The method comprises obtaining a nucleic acid sample from the individual and determining the nucleotide present at one or more of the indicated nucleotide positions, wherein presence of one or more of (a) a G at nucleotide position 942 of SEQ ID NO: 1; (b) a C at nucleotide position 1635 of SEQ ID NO: 1; and (c) an A at nucleotide position 476 of SEQ ID NO: 1 is indicative of increased likelihood of neuropsychiatric disorders in the individual as compared with an appropriate control, e.g., an individual having the variant nucleotide at one or more of said positions. In a particular embodiment the neuropsychiatric disorder is bipolar disorder. In a particular embodiment, the presence of the haplotype formed by the presence of the three reference nucleotides is determined, wherein such presence or occurrence is indicative of increased neuropsychiatric disorders, e.g., bipolar disorder.

The invention further relates to a method of diagnosing or aiding in the diagnosis of a disorder (e.g., a neuropsychiatric disorder) associated with one or more of (a) a G at nucleotide position 942 of SEQ ID NO: 1; (b) a C at nucleotide position 1635 of SEQ ID NO: 1; and (c) an A at nucleotide position 476 of SEQ ID NO: 1 in an individual. The method comprises obtaining a nucleic acid sample from the individual and determining the nucleotide present at one or more of the indicated nucleotide positions, wherein presence of one or more of (a) a T at nucleotide position 942 of SEQ ID NO: 1; (b) a T at nucleotide position 1635 of SEQ ID NO: 1; and (c) a G at nucleotide position 476 of SEQ ID NO: 1 is indicative of decreased likelihood of neuropsychiatric disorders in the individual as compared with an appropriate control, e.g., an individual having the reference nucleotide at said position. In a particular embodiment the neuropsychiatric disorder is bipolar disorder. In a particular embodiment, the presence of the haplotype formed by the presence of the three alternate nucleotides is determined, wherein such presence or occurrence is indicative of decreased neuropsychiatric disorders, e.g., bipolar disorder.

In particular embodiments of the methods described herein, disorders suitable for treatment and diagnosis as described herein include, but are not limited to, bipolar disorder, schizophrenia, schizoaffective disorder, recurrent unipolar depression, hypomania (bipolar II disorder), mood disorders, anxiety disorders, ADHD, Tourette's syndrome, addictive disorders, substance use and abuse disorders, and disorders related to blood pressure. As used herein these disorders are described as neuropsychiatric disorders. In a particular embodiment the neuropsychiatric disorder is bipolar disorder.

In one embodiment, the invention relates to a method for predicting the likelihood that an individual will have a neuropsychiatric disorder (or aiding in the diagnosis of a neuropsychiatric disorder), comprising the steps of obtaining a DNA sample from an individual to be assessed and determining the nucleotide present at one or more of nucleotide positions 476, 942 or 1635 of SEQ ID NO: 1. The presence of the reference nucleotide at one or more of these positions indicates that the individual has a higher likelihood of having a neuropsychiatric disorder than an individual having the variant nucleotide at one or more of these positions, or a higher likelihood of having severe symptomology. In a particular embodiment, the individual is an individual at risk for development of a neuropsychiatric disorder. In a particular embodiment the neuropsychiatric disorder is bipolar disorder. In a particular embodiment, the presence of the haplotype formed by the presence of the three reference nucleotides is determined, wherein such presence or occurrence is indicative of increased neuropsychiatric disorders, e.g., bipolar disorder.

The invention further relates to a method of diagnosing or aiding in the diagnosis of a disorder (e.g., a neuropsychiatric disorder) associated with the presence of one or more of (a) an alanine at amino acid position 304 of SEQ ID NO: 2; and (b) an arginine at amino acid position 535 of SEQ ID NO: 2 in an individual. The method comprises obtaining a biological sample containing the DBH protein or relevant portion thereof from the individual and determining the amino acid present at one or more of the indicated amino acid positions, wherein presence of one or more of (a) an alanine at amino acid position 304 of SEQ ID NO: 2; or (b) an arginine at amino acid position 535 of SEQ ID NO: 2 is indicative of increased likelihood of neuropsychiatric disorders in the individual as compared with an appropriate control, e.g., an individual having the variant amino acid at one or more of said positions. In a particular embodiment the neuropsychiatric disorder is bipolar disorder.

The invention further relates to a method of diagnosing or aiding in the diagnosis of a disorder associated with one or more of (a) an alanine at amino acid position 304 of SEQ ID NO: 2; and (b) an arginine at amino acid position 535 of SEQ ID NO: 2 in an individual. The method comprises obtaining a biological sample from containing the DBH protein or relevant portion thereof from the individual and determining the amino acid present at one or more of the indicated amino acid positions, wherein presence of one or more of (a) a serine at amino acid position 304 of SEQ ID NO: 2; or (b) a cysteine at amino acid position 535 of SEQ ID NO: 2 is indicative of decreased likelihood of neuropsychiatric disorders in the individual as compared with an appropriate control, e.g., an individual having the reference amino acid at said position. In a particular embodiment the neuropsychiatric disorder is bipolar disorder.

In one embodiment, the invention relates to a method for predicting the likelihood that an individual will have a neuropsychiatric disorder (or aiding in the diagnosis of a neuropsychiatric disorder), comprising the steps of obtaining a biological sample comprising the DBH protein or relevant portion thereof from an individual to be assessed and determining the amino acid present at one or more of amino acid positions 304 or 535 of SEQ ID NO: 2. The presence of the reference amino acid at one or more of these positions indicates that the individual has a higher likelihood of having a neuropsychiatric disorder than an individual having the variant amino acid at one or more of these positions, or a higher likelihood of having severe symptomology. In a particular embodiment, the individual is an individual at risk for development of a neuropsychiatric disorder. In a particular embodiment the neuropsychiatric disorder is bipolar disorder.

In another embodiment, the invention relates to pharmaceutical compositions comprising a variant DBH gene product, or active portion thereof, for use in the treatment of neuropsychiatric disorders. The invention further relates to the use of agonists and antagonists of DBH activity for use in the treatment of neuropsychiatric disorders. The invention also relates to the use of a nucleic acid molecule encoding a variant DBH gene product for use in the treatment of neuropsychiatric disorders.

BRIEF DESCRIPTION OF THE DRAWINGS

FIGS. 1A–C show the reference nucleotide (SEQ ID NO: 1) and amino acid (SEQ ID NO: 2) sequences for the DBH gene and gene product.

FIG. 2 shows the results of the DBH association study carried out as described herein (alleles shown are the reference alleles for the indicated polymorphism).

DETAILED DESCRIPTION OF THE INVENTION

Work described herein relates to the discovery of an association between the dopamine beta-hydroxylase (DBH) gene and neuropsychiatric disorders, particularly bipolar disorder. Specifically, it has been discovered that a haplotype formed by alleles of three single nucleotide poymorphisms (SNPs) in the coding region of the DBH gene is transmitted significantly more often from parents to children with bipolar disorder than would be expected by chance. This result has been obtained in two independent family-based samples and is highly statistically significant. A trio included two parents and an offspring diagnosed as having bipolar disorder according to the American Psychiatric Association's Diagnostic and Statistical Manual of Mental Disorders. In the first study of 133 trios formed by a bipolar proband and his/her parents, a haplotype formed by the more common allele of each of three SNPs (DBHu1, DBHu2 and DBHp444a) was transmitted from heterozygous parents (46/25) with a p-value of 0.01 (see FIG. 2). A similar result has been observed in a second sample of 83 trios for the identical haplotype with a p-value of 0.002. This independently confirms the previous observation. Thus, it appears that the less common allele (the variant allele) of each of the three SNPs may contribute to protection or reduction in symptomology with respect to neuropsychiatric disorders, while the more common allele (the reference allele) of each of the three SNPs may predispose an individual to a neuropsychiatric disorder or to increased symptomology of these disorders. The association is particularly strong when two or more of the alleles are considered in combination, and strongest when all three alleles are considered in combination. Alternatively, these particular polymorphisms may belong to a group of two or more polymorphisms in the DBH gene which contributes to the presence, absence, or severity of neuropsychiatric disorders.

The relevant SNPs in the DBH gene, with reference to SEQ ID NO: 1 shown in FIG. 1, are as follows:

DBHu1: a change from G to T at nucleotide position 942, resulting in a missense amino acid mutation from alanine to serine at amino acid 304;

DBHu2: a change from C to T at nucleotide position 1635, resulting in a missense amino acid alteration from arginine to cysteine at amino acid 535; and DBHp444a: a change from A to G at nucleotide position 476, which is a silent mutation resulting in no change in amino acid sequence (glutamine at amino acid 148).

Thus, the reference nucleotide for DBHu1 is G, the reference nucleotide for DBHu2 is C, and the reference nucleotide for DBHp444a is A. The variant nucleotide for DBHu1 is T, the variant nucleotide for DBHu2 is T, and the variant nucleotide for DBHp444a is G. Additionally, the reference amino acid for DBHu1 is alanine, and the reference amino acid for DBHu2 is arginine. The variant amino acid for DBHu1 is serine, and the variant amino acid for DBHu2 is cysteine.

The DBH gene encodes an enzyme whose activity converts the biogenic amine dopamine, a potent neurotransmitter implicated in psychosis, to a second biogenic amine, norepinephrine (adrenaline), which has been implicated in the control of blood pressure. The literature contains observations that DBH activity is bimodal and that the low activity form may be associated with a variety of neuropsychiatric conditions including depression, psychosis, and bipolar disorder. There is, however, no genetic explanation for the bimodal distribution in activity. The haplotype identified as described herein is formed by two missense SNPs and a silent SNP at an exon/intron junction, each of which, either singly or in combination, might explain the observations regarding psychosis. Furthermore, the level of DBH activity has also been associated with blood pressure. Targeting these SNPs may allow the modulation of the relative levels of dopamine and norepinephrine both centrally and peripherally, and thus provide novel drug targets for neuropsychiatric disease and blood pressure control, as well as diagnostic tests for susceptibility to neuropsychiatric disorders.

As used herein, the term "polymorphism" refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair, in which case it is referred to as a single nucleotide polymorphism (SNP).

Thus, the invention relates to a method for predicting the likelihood that an individual will have a neuropsychiatric disorder, or for aiding in the diagnosis of a neuropsychiatric disorder, or predicting the likelihood of having reduced symptomology associated with a neuropsychiatric disorder, comprising the steps of obtaining a DNA sample from an individual to be assessed and determining the nucleotide present at one or more of nucleotide positions 476, 942 and 1635 of the DBH gene. In a preferred embodiment, the nucleotides present at two or more of these nucleotide positions are determined, and in a particularly preferred embodiment the nucleotides present at all three nucleotide positions are determined. In one embodiment the DBH gene has the nucleotide sequence of SEQ ID NO: 1. The presence of one or more of a G (the reference nucleotide) at position 942, a C (the reference nucleotide) at position 1635, or an A (the reference nucleotide) at position 476 indicates that the individual has a greater likelihood of having a neuropsychiatric disorder, or a greater likelihood of having severe symptomology associated with a neuropsychiatric disorders, than if that individual had the variant nucleotide at one or more of these positions. Conversely, the presence of one or more of a T (the variant nucleotide) at position 942, a T (the variant nucleotide) at position 1635, or a G (the variant nucleotide) at position 476 indicates that the individual has a reduced likelihood of having a neuropsychiatric disorder or a likelihood of having reduced symptomology associated with a neuropsychiatric disorder than if that individual had the reference nucleotide at one or more of these positions.

In a particular embodiment, the individual is an individual at risk for development of a neuropsychiatric disorder. In another embodiment the individual exhibits clinical symptomology associated with a neuropsychiatric disorder. In one embodiment, the individual has been clinically diagnosed as having a neuropsychiatric disorder. In a preferred embodiment, the neuropsychiatric disorder is bipolar disorder.

The genetic material to be assessed can be obtained from any nucleated cell from the individual. For assay of genomic DNA, virtually any biological sample (other than pure red blood cells) is suitable. For example, convenient tissue samples include whole blood, semen, saliva, tears, urine, fecal material, sweat, skin and hair. For assay of cDNA or mRNA, the tissue sample must be obtained from an organ in which the target nucleic acid is expressed. For example, cells from the central nervous system (such as cells of the hippocampus) are suitable sources for obtaining cDNA for the DBH gene.

Many of the methods described herein require amplification of DNA from target samples. This can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA,* 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The nucleotide which occupies the polymorphic site of interest (e.g., nucleotide positions 476, 942 and 1635 in the DBH gene) can be identified by a variety of methods, such as Southern analysis of genomic DNA; direct mutation analysis by restriction enzyme digestion; Northern analysis of RNA; denaturing high pressure liquid chromatography (DHPLC); gene isolation and sequencing; hybridization of an allele-specific oligonucleotide with amplified gene products; single base extension (SBE). In a preferred embodiment, determination of the allelic form of DBH is carried out using SBE-FRET methods as described herein, or using chip-based oligonucleotide arrays as described herein. A sampling of suitable procedures is discussed below in turn.

1. Allele-Specific Probes

The design and use of allele-specific probes for analyzing polymorphisms is described by e.g., Saiki et al., *Nature* 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Hybridizations are usually performed under stringent conditions, for example, at a salt concentration of no more than 1 M and a temperature of at least 25° C. For example, conditions of 5X SSPE (750 mM NaCl, 50 mM NaPhosphate, 5 mM EDTA, pH 7.4) and a temperature of 25–30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some examples of which are described in WO 95/11995. WO 95/11995 also describes subarrays that are optimized for detection of a variant form of a precharacterized polymorphism. Such a subarray contains probes designed to be complementary to a second reference sequence, which is an allelic variant of the first reference sequence. The second group of probes is designed by the same principles, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarity. See Gibbs, *Nucleic Acid Res.* 17, 2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

4. Direct-Sequencing

The direct analysis of the sequence of polymorphisms of the present invention can be accomplished using either the dideoxy chain termination method or the Maxam-Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., *PCR Technology, Principles and Applications for DNA Amplification*, (W. H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., *Proc. Nat. Acad. Sci.* 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

7. Single-Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method, such as that described by Chen et al., (*PNAS* 94:10756–61 (1997), incorporated herein by reference) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

The invention also relates to a method for predicting the likelihood that an individual will have a neuropsychiatric disorder, or for aiding in the diagnosis of a neuropsychiatric disorder, or predicting the likelihood of having reduced symptomology associated with a neuropsychiatric disorder, comprising the steps of obtaining a biological sample comprising DBH protein or relevant portion thereof from an individual to be assessed and determining the amino acid present at one or more of amino acid positions 304 and 535 of the DBH gene. In a preferred embodiment, the amino acids present at both of these amino acid positions are determined. In one embodiment the DBH protein has the amino acid sequence of SEQ ID NO: 2. As used herein, the term "relevant portion" of the DBH protein is intended to encompass any portion of the protein which comprises one or more of the relevant amino acid positions. The presence of one or more of an alanine (the reference amino acid) at position 304, or an arginine (the reference amino acid) at position 535 indicates that the individual has a greater likelihood of having a neuropsychiatric disorder, or a greater likelihood of having severe symptomology associated with a neuropsychiatric disorders, than if that individual had the variant amino acid at one or more of these positions. Conversely, the presence of one or more of a serine (the variant amino acid) at position 304, or a cysteine (the variant amino acid) at position 535 indicates that the individual has a reduced likelihood of having a neuropsychiatric disorder or a likelihood of having reduced symptomology associated with a neuropsychiatric disorder than if that individual had the reference amino acid at one or more of these positions. In a preferred embodiment the identity of the amino acid at both position 304 and 535 is assessed.

In a particular embodiment, the individual is an individual at risk for development of a neuropsychiatric disorder. In another embodiment the individual exhibits clinical symptomology associated with a neuropsychiatric disorder. In one embodiment, the individual has been clinically diagnosed as having a neuropsychiatric disorder. In a preferred embodiment, the neuropsychiatric disorder is bipolar disorder.

In this embodiment of the invention, the biological sample contains protein molecules from the test subject. In vitro techniques for detection of protein include enzyme linked immunosorbent assays (ELISAs), Western blots, immunoprecipitations and immunofluorescence. Furthermore, in vivo techniques for detection of protein include introducing into a subject a labeled anti-protein antibody. For example, the antibody can be labeled with a radioactive marker whose presence and location in a subject can be detected by standard imaging techniques. Polyclonal and/or monoclonal antibodies that specifically bind to variant gene products but not to corresponding reference gene products, and vice versa, are also provided. Antibodies can be made by injecting mice or other animals with the variant gene product or synthetic peptide fragments thereof comprising the variant portion. Monoclonal antibodies are screened as are described, for example, in Harlow & Lane, *Antibodies, A Laboratory Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

The polymorphisms of the invention may be associated with neuropsychiatric disorders in different ways. The polymorphisms may exert phenotypic effects indirectly via influence on replication, transcription, and translation. Additionally, the described polymorphisms may predispose an individual to a distinct mutation that is causally related to a certain phenotype, such as susceptibility or resistance to neuropsychiatric disorders and related disorders. The discovery of the polymorphisms and their correlation with bipolar disorder facilitates biochemical analysis of the variant and reference forms and the development of assays to characterize the variant and reference forms and to screen for pharmaceutical agents that interact directly with one or another form of the protein. For example, agents can be designed which mimic, agonize or antagonize the activity or level of the reference or variant alleles.

Alternatively, these particular polymorphisms may belong to a group of two or more polymorphisms in the DBH gene which contributes to the presence, absence or severity of neuropsychiatric disorders. An assessment of other polymorphisms within the DBH gene can be undertaken, and the separate and combined effects of these polymorphisms, as well as alterations in other, distinct genes, on the neuropsychiatric disorder phenotype can be assessed. For example, it has been discovered that a polymorphism in the gene for brain-derived neurotrophic factor (BDNF) is negatively correlated with incidence of neuropsychiatric disorders (e.g., bipolar disorder) (see U.S. patent application Ser. No. 09/636,368, filed Aug. 11, 2000, the teachings of which are incorporated herein by reference).

More than one phenotypic trait may be affected. For example, other neuropsychiatric disorders which are believed to be alternate expressions of a bipolar genotype, including variants of schizoaffective disorder, recurrent unipolar depression and hypomania (bipolar II disorder), may also be affected by the DBH polymorphisms described herein. In particular embodiments of the methods of the invention, disorders suitable for treatment and diagnosis as described herein include, but are not limited to, bipolar disorder, schizophrenia, schizoaffective disorder, recurrent unipolar depression, hypomania (bipolar II disorder), mood disorders, anxiety disorders, ADHD, Tourette's syndrome, addictive disorders, substance use and abuse disorders, and disorders related to blood pressure. As used herein these disorders are described as neuropsychiatric disorders. In a particular embodiment the neuropsychiatric disorder is bipolar disorder.

Correlation between a particular phenotype, e.g., the bipolar phenotype, and the presence or absence of a particular allele is performed for a population of individuals who have been tested for the presence or absence of the phenotype. Correlation can be performed by standard statistical methods such as a Chi-squared test and statistically significant correlations between polymorphic form(s) and phenotypic characteristics are noted. For example, a haplotype formed by the more common (reference) allele of each of three DBH SNPs (DBHu1, DBHu2 and DBHp444a) was transmitted from 133 heterozygous parents (46/25) with a p-value of 0.01. A similar result has been observed in a second sample of 83 trios for the identical haplotype with a p-value of 0.002.

This correlation can be exploited in several ways. In the case of a strong correlation between a particular polymorphic form, e.g., the reference allele for DBH, and a disease for which treatment is available, e.g., bipolar disorder, detection of the polymorphic form in an individual may justify immediate administration of treatment, or at least the institution of regular monitoring of the individual. Detection of a polymorphic form correlated with a disorder in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic form and a particular disorder, immediate therapeutic intervention or monitoring may not be justified. Nevertheless, the individual can be motivated to begin simple life-style changes (e.g., therapy or counseling) that can be accomplished at little cost to the individual but confer potential benefits in reducing the risk of conditions to which the individual may have increased susceptibility by virtue of the particular allele. Furthermore, identification of a polymorphic form correlated with enhanced receptiveness to one of several treatment regimes for a disorder indicates that this treatment regimen should be followed for the individual in question.

Furthermore, it may be possible to identify a physical linkage between a genetic locus associated with a trait of interest (e.g., bipolar disorder) and polymorphic markers that are or are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., *Proc. Natl. Acad. Sci.* (USA) 83, 7353–7357 (1986); Lander et al., *Proc. Natl. Acad. Sci.* (USA) 84, 2363–2367 (1987); Donis-Keller et al., *Cell* 51, 319–337 (1987); Lander et al., *Genetics* 121, 185–199 (1989)). Genes localized by linkage can be cloned by a process known as directional cloning. See Wainwright, *Med. J. Australia* 159, 170–174 (1993); Collins, *Nature Genetics* 1, 3–6 (1992).

Linkage studies are typically performed on members of a family, such as the bipolar proband and his/her parents studied as described herein. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., *Science* 245, 1073–1080 (1989); Monaco et al., *Nature* 316, 842 (1985); Yamoka et al., *Neurology* 40, 222–226 (1990); Rossiter et al., *FASEB Journal* 5, 21–27 (1991).

Linkage is analyzed by calculation of LOD (log of the odds) values. A lod value is the relative likelihood of obtaining observed segregation data for a marker and a genetic locus when the two are located at a recombination fraction $\theta$, versus the situation in which the two are not linked, and thus segregating independently (Thompson & Thompson, *Genetics in Medicine* (5th ed, W.B. Saunders Company, Philadelphia, 1991); Strachan, "Mapping the human genome" in *The Human Genome* (BIOS Scientific Publishers Ltd, Oxford), Chapter 4). A series of likelihood ratios are calculated at various recombination fractions ($\theta$), ranging from $\theta=0.0$ (coincident loci) to $\theta=0.50$ (unlinked). Thus, the likelihood at a given value of $\theta$ is: probability of data if loci linked at $\theta$ to probability of data if loci unlinked. The computed likelihoods are usually expressed as the $\log_{10}$ of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of $\theta$ (e.g., LIPED, MLINK (Lathrop, *Proc. Nat. Acad. Sci.* (USA) 81, 3443–3446 (1984)). For any particular lod score, a recombination fraction may be determined from mathematical tables. See Smith et al., *Mathematical tables for research workers in human genetics* (Churchill, London, 1961); Smith, *Ann. Hum. Genet.* 32, 127–150 (1968). The value of $\theta$ at which the lod score is the highest is considered to be the best estimate of the recombination fraction.

Positive lod score values suggest that the two loci are linked, whereas negative values suggest that linkage is less likely (at that value of $\theta$) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of –2 or less is taken as definitive evidence against linkage of the two loci being compared. Negative linkage data are useful in excluding a chromosome or a segment thereof from consideration. The search focuses on the remaining non-excluded chromosomal locations.

In another embodiment, the invention relates to pharmaceutical compositions, including those comprising a variant DBH gene or gene product, for use in the treatment of neuropsychiatric disorders, e.g., bipolar disorder. As used herein, a variant DBH gene product (e.g., protein or polypeptide) is intended to mean gene products which are encoded by a variant allele (comprising one or more variant nucleotides) of the DBH gene. In addition to substantially full-length polypeptides expressed by variant genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures. Variant DBH gene products are also intended to encompass gene products comprising any alteration which has the same effect as that conferred by the variant genotype. For example, pharmaceutical compositions can mimic, agonize or antagonize the level or activity of a variant or reference DBH gene product described herein. Suitable compositions include small molecules, nucleic acid molecules (e.g., antisense molecules) and proteins or polypeptides.

For instance, the variant polypeptide or protein, or fragment thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to the skilled artisan, and will depend on the ultimate pharmaceutical formulation desired. Methods of introduction of exogenous peptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents and treatment regimens.

The invention further pertains to compositions, e.g., vectors, comprising a nucleotide sequence encoding variant DBH gene product. For example, variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like.

It is also contemplated that cells can be engineered to express the variant allele of the invention by gene therapy methods. For example, DNA encoding the variant DBH gene product, or an active fragment or derivative thereof, can be introduced into an expression vector, such as a viral vector, and the vector can be introduced into appropriate cells in an animal. In such a method, the cell population can be engineered to inducibly or constitutively express active variant DBH gene product. In a preferred embodiment, the vector is delivered to the bone marrow, for example as described in Corey et al. (*Science* 244:1275–1281 (1989)).

The invention further relates to the use of compositions (i.e., agonists) which enhance or increase the level or activity of the variant DBH gene product, or a functional portion thereof, for use in the treatment of neuropsychiatric disorders. The invention also relates to the use of compositions (i.e., antagonists) which reduce or decrease the level or activity of the reference DBH gene product, or a functional portion thereof, for use in the treatment of neuropsychiatric disorders. Agonists and antagonists can act directly on the DBH enzyme or upstream or downstream of the DBH enzyme in the cascade of mediators in pathways in which DBH plays a part.

The invention also relates to constructs which comprise a vector into which a sequence of the invention has been inserted in a sense or antisense orientation. For example, a vector comprising a nucleotide sequence which is antisense to the reference DBH allele may be used as an antagonist of the activity of the DBH reference allele. Alternatively, a vector comprising a nucleotide sequence of the DBH variant allele may be used therapeutically to treat neuropsychiatric disorders. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc.

The expression vectors of the invention can be introduced into host cells to thereby produce proteins or peptides, including fusion proteins or peptides, encoded by nucleic acids as described herein. The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian, e.g., human, cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a nucleic acid of the invention can be expressed in bacterial cells (e.g., *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*supra*), and other laboratory manuals.

A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid of the invention (e.g., a variant or reference DBH allele) have been introduced. Such host cells can then be used to create non-human transgenic animals in which exogenous nucleotide sequences have been introduced into their genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid of the invention into the male pronuclei of a fertilized oocyte, e.g., by microinjection, retroviral infection, and allowing the oocyte to develop in a pseudopregnant female foster animal. The sequence can be introduced as a transgene into the genome of a non-human animal. Intronic sequences and polyadenylation signals can also be included in the transgene to increase the efficiency of expression of the transgene. A tissue-specific regulatory sequence(s) can be operably linked to the transgene to direct expression of a polypeptide in particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA in tissues or cells of the animals. A transgenic founder animal can then be used to breed additional animals carrying the transgene. Moreover, transgenic animals carrying a transgene encoding the transgene can further be bred to other transgenic animals carrying other transgenes.

The invention also relates to the use of the variant and wildtype gene products to guide efforts to identify the causative mutation for neuropsychiatric disorders or to identify or synthesize agents useful in the treatment of neuropsychiatric disorders, e.g., bipolar disorder. For example, amino acids that are essential for function can be identified by methods known in the art, such as site-directed mutagenesis or alanine-scanning mutagenesis (Cunningham et al, *Science*, 244:1081–1085 (1989)). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al., *J. Mol. Biol.*, 224:899–904 (1992); de Vos et al. *Science*, 255:306–312 (1992)).

Another aspect of the invention pertains to monitoring the influence of agents (e.g., drugs, compounds) on the expression or activity of proteins of the invention in clinical trials. An exemplary method for detecting the presence or absence of proteins or nucleic acids of the invention in a biological sample involves obtaining a biological sample from a test subject and contacting the biological sample with a compound or an agent capable of detecting the protein, or nucleic acid (e.g., mRNA, genomic DNA) that encodes the protein, such that the presence of the protein or nucleic acid is detected in the biological sample. A preferred agent for detecting mRNA or genomic DNA is a labeled nucleic acid probe capable of hybridizing to mRNA or genomic DNA sequences described herein, preferably in an allele-specific manner. The nucleic acid probe can be, for example, a full-length nucleic acid, or a portion thereof, such as an oligonucleotide of at least 15, 30, 50, 100, 250 or 500 nucleotides in length and sufficient to specifically hybridize under stringent conditions to appropriate mRNA or genomic DNA. Other suitable probes for use in the diagnostic assays of the invention are described herein. Other agents for use in the diagnostic assays of the invention are antibodies described herein which bind specifically to the reference or variant DBH protein or polypeptide. These antibodies can be used to detect the presence or absence of the reference or variant DBH protein or polypeptide.

The invention also encompasses kits for detecting the presence of proteins or nucleic acid molecules of the invention in a biological sample. For example, the kit can comprise a labeled compound or agent (e.g., nucleic acid molecule, antibody, etc.) capable of detecting protein, DNA or mRNA in a biological sample; means for determining the amount of in the sample; and means for comparing the amount of in the sample with a standard. The compound or agent can be packaged in a suitable container. The kit can further comprise instructions for using the kit to detect protein or nucleic acid. In a preferred embodiment the labeled compound or agent detects either the alternate or reference form of the protein, DNA or mRNA, but not both.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining the likelihood of bipolar disorder in an individual, comprising determining the nucleotide present at nucleotide positions 476, 942, and 1635 of the dopamine beta-hydroxylase gene in a nucleic acid sample obtained from an individual, wherein the individual is an offspring of a parent having bipolar disorder, wherein presence of a haplotype consisting of an A at nucleotide position 476, a G at nucleotide position 942, and a C at nucleotide position 1635 is indicative of an increased likelihood of bipolar disorder in the individual as compared with an individual who does not have said haplotype.

2. The method of claim 1, wherein the dopamine beta-hydroxylase gene has the nucleotide sequence of SEQ ID NO: 1.

3. A method of determining the likelihood of bipolar disorder in an individuals comprising determining the nucleotide present at nucleotide positions 476, 942, and 1635 of the dopamine beta-hydroxylase gene in a nucleic acid sample obtained from an individual, wherein the individual is an offspring of a parent having bipolar disorder, wherein presence of a haplotype consisting of a G at nucleotide position 476, a T at nucleotide position 942, and a T at nucleotide position 1635 is indicative of a decreased likelihood of bipolar disorder in the individual as compared with an individual who does not have said haplotype.

4. The method according to claim 3, wherein the dopamine beta-hydroxylase gene has the nucleotide sequence of SEQ ID NO: 1.

* * * * *

SEQUENCE LISTING

<160> NUMBER OF SEQ ID NOS: 2

<210> SEQ ID NO 1
<211> LENGTH: 2725
<212> TYPE: DNA
<213> ORGANISM: Homo sapiens

<400> SEQUENCE: 1

| | | | | | |
|---|---|---|---|---|---|
| tcagtcgctg | ggccagcctg | cccggcccca | gcatgcggga | ggcagccttc atgtacagca | 60 |
| cagcagtggc | catcttcctg | gtcatcctgg | tggccgcact | gcagggctcg gctcccgtg | 120 |
| agagccccct | cccctatcac | atcccctgg | acccggaggg | gtccctggag ctctcatgga | 180 |
| atgtcagcta | cacccaggag | gccatccatt | tccagctcct | ggtgcggagg ctcaaggctg | 240 |
| gcgtcctgtt | tgggatgtcc | gaccgtggcg | agcttgagaa | cgcagatctc gtggtgctct | 300 |
| ggaccgatgg | ggacactgcc | tattttgcgc | acgcctggag | tgaccagaag gggcagatcc | 360 |
| acctggatcc | ccagcaggac | taccagctgc | tgcaggtgca | gaggaccca gaaggcctga | 420 |
| ccctgctttt | caagaggccc | tttggcacct | gcgaccccaa | ggattacctc attgaagacg | 480 |
| gcactgtcca | cttggtctac | gggatcctgg | aggagccgtt | ccggtcactg gaggccatca | 540 |
| acggctcggg | cctgcagatg | gggctgcaga | gggtgcagct | cctgaagccc aatatccccg | 600 |
| aaccggagtt | gccctcagac | gcgtgcacca | tggaggtcca | agctcccaat atccagatcc | 660 |
| ccagccagga | gaccacgtac | tggtgctaca | ttaaggagct | tccaaagggc ttctctcggc | 720 |
| accacattat | caagtacgag | cccatcgtca | ccaagggcaa | tgaggccctt gtccaccaca | 780 |
| tggaagtctt | ccagtgcgcc | cccgagatgg | acagcgtccc | ccacttcagc gggccctgcg | 840 |
| actccaagat | gaaacccgac | cgcctcaact | actgccgcca | cgtgctggcc gcctgggccc | 900 |
| tgggtgccaa | gcatttttac | tacccagagg | aagccggcct | tgccttcggg ggtccagggt | 960 |
| cctccagata | tctccgcctg | gaagttcact | accacaaccc | actggtgata aaggacgaa | 1020 |
| acgactcctc | aggcatccgc | ttgtactaca | cagccaagct | gcggcgcttc aacgcgggga | 1080 |
| tcatggagct | gggactggtg | tacacgccag | tgatggccat | tccaccacgg agaccgcct | 1140 |
| tcatcctcac | tggctactgc | acggacaagt | gcacccagct | ggcactgcct ccctccggga | 1200 |
| tccacatctt | cgcctctcag | ctccacacac | acctgactgg | gagaaaggtg gtcacagtgc | 1260 |
| tggtccggga | cggccgggag | tgggagatcg | tgaaccagga | caatcactac agccctcact | 1320 |
| tccaggagat | ccgcatgttg | aagaaggtcg | tgtcggtcca | tccgggagat gtgctcatca | 1380 |
| cctcctgcac | gtacaacacg | gaagaccggg | agctggccac | agtgggggc ttcgggatcc | 1440 |
| tggaggagat | gtgtgtcaac | tacgtgcact | actaccccca | gacgcagctg gagctctgca | 1500 |
| agacggctgt | ggacgccggc | ttcctgcaga | gtacttcca | cctcatcaac aggttcaaca | 1560 |
| acgaggatgt | ctgcacctgc | cctcaggcgt | ccgtgtctca | gcagttcacc tctgttccct | 1620 |
| ggaactcctt | caaccgcgac | gtactgaagg | ccctgtacag | cttcgcgccc atctccatgc | 1680 |
| actgcaacaa | gtcctcagcc | gtccgcttcc | agggtgaatg | gaacctgcag ccctgccca | 1740 |
| aggtcatctc | cacactggaa | gagcccaccc | cacagtgccc | caccagccag ggccgaagcc | 1800 |
| ctgctggccc | caccgttgtc | agcattggtg | ggggcaaagg | ctgagggggg acctactcct | 1860 |
| cccctcctc | catgctgtcc | ctgtgggctc | acaccggcac | tgtgcactct actctgcgac | 1920 |
| gatcccatg | gaacagccct | gcacgccag | gatgaagggg | ccagaccacg ccctgcctg | 1980 |
| agaccacggt | ccaatccagc | cttcttcccc | cagggtcccc | tgcatggctg agagggtgtg | 2040 |

-continued

```
ggtgccctgt tgacctaccc tggaccgagt ggaccacgac ctcgtccatt taaacccggc   2100
tgactcagtg cagggacagc ccgcacagtg gtccagggtc cagccctccg ccagccctgt   2160
tccgcctcac tgggtgtggc ctggcttctg gacaggcac catgctgggc cggggtgtgg    2220
aatcaccggg aacgccccg ccccgcccc gctgctcccg gtgtgcagcg ggtgcgggtg     2280
ccgcttaaac atttccctgc tgagtggctc gtgtttcaca gtgggcggct tccctgcgac   2340
ggaggcagga ccaggcattt agctagttag agactcgcct gggaaattgc tccattcctg   2400
agtaaacaga tattttcgcc cacctaaagg gaagccctga caacaactat caccaaaaga   2460
cgaggcggca agatccagc ggggcttctg gcgccggtt ccacgtgggg tggaattatt     2520
agcaccagct tgcttctctg ccggtggggc cagcgctgaa cagaccgggg tggagtcagg   2580
gctgtgcttt ccgcgtggtt ctgccactta gggagtgtgc cttgggcggg ccatttcaca   2640
ttcctgaccc tcactttttct catctgtaaa accaggctga tgccgtgcgg gctaatgagc  2700
caataaagct cacacttggg ctggc                                        2725
```

<210> SEQ ID NO 2
<211> LENGTH: 603
<212> TYPE: PRT
<213> ORGANISM: Homo sapiens

<400> SEQUENCE: 2

```
Met Arg Glu Ala Ala Phe Met Tyr Ser Thr Ala Val Ala Ile Phe Leu
 1               5                  10                  15

Val Ile Leu Val Ala Ala Leu Gln Gly Ser Ala Pro Arg Glu Ser Pro
                20                  25                  30

Leu Pro Tyr His Ile Pro Leu Asp Pro Glu Gly Ser Leu Glu Leu Ser
            35                  40                  45

Trp Asn Val Ser Tyr Thr Gln Glu Ala Ile His Phe Gln Leu Leu Val
        50                  55                  60

Arg Arg Leu Lys Ala Gly Val Leu Phe Gly Met Ser Asp Arg Gly Glu
65                  70                  75                  80

Leu Glu Asn Ala Asp Leu Val Val Leu Trp Thr Asp Gly Asp Thr Ala
                85                  90                  95

Tyr Phe Ala Asp Ala Trp Ser Asp Gln Lys Gly Gln Ile His Leu Asp
            100                 105                 110

Pro Gln Gln Asp Tyr Gln Leu Leu Gln Val Gln Arg Thr Pro Glu Gly
        115                 120                 125

Leu Thr Leu Leu Phe Lys Arg Pro Phe Gly Thr Cys Asp Pro Lys Asp
    130                 135                 140

Tyr Leu Ile Glu Asp Gly Thr Val His Leu Val Tyr Gly Ile Leu Glu
145                 150                 155                 160

Glu Pro Phe Arg Ser Leu Glu Ala Ile Asn Gly Ser Gly Leu Gln Met
                165                 170                 175

Gly Leu Gln Arg Val Gln Leu Leu Lys Pro Asn Ile Pro Glu Pro Glu
            180                 185                 190

Leu Pro Ser Asp Ala Cys Thr Met Glu Val Gln Ala Pro Asn Ile Gln
        195                 200                 205

Ile Pro Ser Gln Glu Thr Thr Tyr Trp Cys Tyr Ile Lys Glu Leu Pro
    210                 215                 220

Lys Gly Phe Ser Arg His His Ile Ile Lys Tyr Glu Pro Ile Val Thr
225                 230                 235                 240

Lys Gly Asn Glu Ala Leu Val His His Met Glu Val Phe Gln Cys Ala
```

-continued

```
                        245                 250                 255
Pro Glu Met Asp Ser Val Pro His Phe Ser Gly Pro Cys Asp Ser Lys
            260                 265                 270

Met Lys Pro Asp Arg Leu Asn Tyr Cys Arg His Val Leu Ala Ala Trp
            275                 280                 285

Ala Leu Gly Ala Lys Ala Phe Tyr Pro Glu Glu Ala Gly Leu Ala
            290                 295                 300

Phe Gly Gly Pro Gly Ser Ser Arg Tyr Leu Arg Leu Glu Val His Tyr
305                 310                 315                 320

His Asn Pro Leu Val Ile Glu Gly Arg Asn Asp Ser Ser Gly Ile Arg
                325                 330                 335

Leu Tyr Tyr Thr Ala Lys Leu Arg Arg Phe Asn Ala Gly Ile Met Glu
            340                 345                 350

Leu Gly Leu Val Tyr Thr Pro Val Met Ala Ile Pro Pro Arg Glu Thr
            355                 360                 365

Ala Phe Ile Leu Thr Gly Tyr Cys Thr Asp Lys Cys Thr Gln Leu Ala
    370                 375                 380

Leu Pro Pro Ser Gly Ile His Ile Phe Ala Ser Gln Leu His Thr His
385                 390                 395                 400

Leu Thr Gly Arg Lys Val Val Thr Val Leu Val Arg Asp Gly Arg Glu
                405                 410                 415

Trp Glu Ile Val Asn Gln Asp Asn His Tyr Ser Pro His Phe Gln Glu
                420                 425                 430

Ile Arg Met Leu Lys Lys Val Val Ser Val His Pro Gly Asp Val Leu
            435                 440                 445

Ile Thr Ser Cys Thr Tyr Asn Thr Glu Asp Arg Glu Leu Ala Thr Val
    450                 455                 460

Gly Gly Phe Gly Ile Leu Glu Glu Met Cys Val Asn Tyr Val His Tyr
465                 470                 475                 480

Tyr Pro Gln Thr Gln Leu Glu Leu Cys Lys Thr Ala Val Asp Ala Gly
            485                 490                 495

Phe Leu Gln Lys Tyr Phe His Leu Ile Asn Arg Phe Asn Asn Glu Asp
            500                 505                 510

Val Cys Thr Cys Pro Gln Ala Ser Val Ser Gln Gln Phe Thr Ser Val
    515                 520                 525

Pro Trp Asn Ser Phe Asn Arg Asp Val Leu Lys Ala Leu Tyr Ser Phe
    530                 535                 540

Ala Pro Ile Ser Met His Cys Asn Lys Ser Ser Ala Val Arg Phe Gln
545                 550                 555                 560

Gly Glu Trp Asn Leu Gln Pro Leu Pro Lys Val Ile Ser Thr Leu Glu
                565                 570                 575

Glu Pro Thr Pro Gln Cys Pro Thr Ser Gln Gly Arg Ser Pro Ala Gly
            580                 585                 590

Pro Thr Val Val Ser Ile Gly Gly Lys Gly
            595                 600
```